(12) United States Patent
Tampieri et al.

(10) Patent No.: US 11,167,097 B2
(45) Date of Patent: *Nov. 9, 2021

(54) DRY POWDER INHALER AND INHALATION ACTUATED MECHANISM THEREOF

(71) Applicant: Chiesi Farmaceutici S.p.A., Parma (IT)

(72) Inventors: Valerio Tampieri, Parma (IT); Lorenzo Zuccheri, Parma (IT); Emiliano Ilandi, Parma (IT); Alice Campanini, Parma (IT); Irene Pasquali, Parma (IT); Patrick Gerard Linnane, Parma (IT); Nicholas Lee Hawson, Parma (IT); David Gale, Parma (IT); Joanne Garrad, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 325 days.

This patent is subject to a terminal disclaimer.

(21) Appl. No.: 16/269,031

(22) Filed: Feb. 6, 2019

(65) Prior Publication Data

US 2019/0167925 A1 Jun. 6, 2019
US 2020/0230331 A9 Jul. 23, 2020

Related U.S. Application Data

(63) Continuation of application No. 14/755,658, filed on Jun. 30, 2015, now Pat. No. 10,238,819.

(30) Foreign Application Priority Data

Jun. 30, 2014 (EP) .................................. 14175021

(51) Int. Cl.
*A61M 15/00* (2006.01)

(52) U.S. Cl.
CPC .... *A61M 15/0021* (2014.02); *A61M 15/0065* (2013.01); *A61M 15/0075* (2014.02);
(Continued)

(58) Field of Classification Search
CPC .......... A61M 15/0021; A61M 15/0065; A61M 15/0075; A61M 15/0091
See application file for complete search history.

(56) References Cited

U.S. PATENT DOCUMENTS 6,029,662 A 2/2000 Marcon
2004/0025870 A1* 2/2004 Harrison ........... A61M 15/0091
128/202.17
(Continued)

FOREIGN PATENT DOCUMENTS

EP 1 386 630 A1 2/2004
EP 2617448 A1 * 7/2013 ........ A61M 15/0091
(Continued)

*Primary Examiner* — Kathryn E Ditmer
(74) *Attorney, Agent, or Firm* — Mintz Levin Cohn Ferris Glovsky and Popeo, P.C.; Peter F. Corless; Steven M. Jensen

(57) ABSTRACT

A flap (20) for an inhalation actuated mechanism (18) of a powder inhaler (1) comprises a base member (29), a skirt structure (24) projecting from a surface of the base member (29), and a coupling portion (21) to be coupled to a resilient member (40') of the inhalation actuated mechanism (18).

20 Claims, 5 Drawing Sheets

(52) U.S. Cl.
CPC ..... *A61M 15/0091* (2013.01); *A61M 15/0025* (2014.02); *A61M 2202/062* (2013.01); *A61M 2202/064* (2013.01); *A61M 2206/16* (2013.01)

(56) References Cited

U.S. PATENT DOCUMENTS

| | | |
|---|---|---|
| 2004/0107962 A1 | 6/2004 | Harrison et al. |
| 2004/0237961 A1 | 12/2004 | Snow et al. |
| 2005/0092323 A1* | 5/2005 | Frietsch ............ A61M 15/0091 128/203.15 |
| 2005/0183723 A1 | 8/2005 | Pinon et al. |
| 2006/0150971 A1 | 7/2006 | Lee et al. |
| 2006/0231093 A1 | 10/2006 | Burge et al. |

FOREIGN PATENT DOCUMENTS

| | | | |
|---|---|---|---|
| EP | 2617448 A1 | 7/2013 | |
| FR | 2701653 A1 | 8/1994 | |
| JP | 2006-062449 A | 3/2006 | |
| WO | 93/24167 A1 | 12/1993 | |
| WO | 2004/041339 A2 | 5/2004 | |
| WO | 2006062449 A1 | 6/2006 | |
| WO | WO-2006062449 A1 * | 6/2006 | ........ A61M 15/0078 |
| WO | 2007/066140 A1 | 6/2007 | |
| WO | 2013/107640 A1 | 7/2013 | |

\* cited by examiner

DRY POWDER INHALER AND INHALATION ACTUATED MECHANISM THEREOF

CROSS-REFERENCE TO RELATED APPLICATION(S)

This application is a continuation of copending application U.S. Ser. No. 14/755,658, filed on Jun. 30, 2015, which claims under 35 U.S.C. § 119(a) the benefit of European Application No. 14 175 021.6, filed Jun. 30, 2014, the entire contents of which are incorporated by reference herein.

BACKGROUND

(a) Technical Field

The present invention relates to a flap for an inhalation actuated mechanism of a powder inhaler and a corresponding powder inhaler.

(b) Description of Related Art

Powder inhalers are devices for dispensing a powdered medicament preparation by inhalation. The administering of a powdered medicament preparation by inhalation from an inhaler is commonly known.

EP 1 386 630 B1 by the applicant of this patent application discloses a portable multiple-dose device without propellant gas, which is equipped with a metering member for dispensing doses from a medicament container. The device is based on a centripetal force for achieving a more effective pulverization/deagglomeration of the particles of the micronized powdered medicament from a coarser carrier in such a manner that the penetration of the medicament into the lungs of a user or patient is improved and the adhesion of the powdered medicament to the upper respiratory passages is reduced for alleviating possible side effects caused thereby. The device of EP 1 386 630 B1 comprises a protective member, preferably a thin plate sliding on the metering member, the protective member being moveable between a closed position, in which it at least covers a dosing recess of the metering member to prevent the powdered medicament contained in the dosing recess from entering into an inhalation channel of the powder inhaler, and an open position, in which the protective member does not cover the dosing recess, so that the dosing recess is exposed to the inhalation channel to enable inhalation of the dose of the powdered medicament contained in the dosing recess. The protective member prevents a metered dose of the powdered medicament from falling out of the dosing recess, thereby preventing an unintentional loss of the powdered medicament.

The protective member is preferably automatically withdrawn and moved from its closed position into its open position upon an inhalation process. Thus, the powder inhaler can be used in a variety of orientations, even upside down when the user or patient is lying in a bed, for example.

In order to automatically withdraw the protective member from its closed position and move it into its open position, the powder inhaler of EP 1 386 630 B1 comprises an inhalation actuated mechanism which is designed and coupled to the protective member such that it moves the protective member into its open position if the inhalation suction force of the respective user exceeds a predetermined value. The inhalation actuation mechanism is further constructed such that it automatically returns the protective member into its closed position after the respective inhalation process has properly been completed.

The present invention especially relates to a further development of this inhalation actuated mechanism, so that in the following the inhalation actuated mechanism known from EP 1 386 630 B1 will be described in more detail. As the further configuration of the powder inhaler of the present invention may be similar or even identical to the powder inhaler known from EP 1 386 630 B1, the disclosure of EP 1 386 630 B1 is hereby incorporated by reference in its entirety.

FIG. 4 shows a cross-sectional view of the powder inhaler known from EP 1 386 630 B1.

As shown in FIG. 4, the powder inhaler comprises a casing with a lower shell 1 and an integral cover 2 being pivotably or rotatably coupled to the lower shell 1. The integral cover 2 can be opened to reveal a mouthpiece 3 with which a user can inhale a powdered medicament. The powder inhaler comprises a dosing sub-assembly comprising a container or reservoir 4 for storing the powdered medicament, the metering member 5, and a deagglomerator arrangement 10 to be coupled to the inhalation channel 9 of the mouthpiece 3. The deagglomerator arrangement 10 is constructed such that it generates a cyclonic airflow resulting in a strong velocity gradient.

The metering member 5 is preferably provided in the form of a shuttle or slide which is moveable in the horizontal direction and has the dosing recess 15 in the form of a dosing cup formed in a longitudinal middle region thereof. The dosing recess 15 is provided for metering a dose of the powdered medicament and for transporting the dose from a filling position underneath the container 4, in which the dosing recess 15 is in alignment with an opening at the bottom of the container 4, to an inhalation position underneath the deagglomerator arrangement 10, in which the dosing recess 15 is in alignment with the inhalation channel 9.

The powdered medicament is stored in a medicament chamber of the container 4. Furthermore, the container 4 may comprise a desiccant chamber storing a desiccant for absorbing moisture that may have entered the medicament chamber. As indicated in FIG. 4, the desiccant chamber may be separated from the medicament chamber by a permeable membrane. The medicament chamber has a gradually decreasing cross-section diameter from its top to its bottom so that the medicament chamber of the container 4 is shaped like a funnel supporting an easier filling of the dosing recess 15.

The metering member 5 is coupled to the cover 2 by a coupling mechanism, e.g., a coupling mechanism comprising profiled cam tracks, which is constructed such that opening the cover 2 causes the metering member 5 to move forward from its filling position to its inhalation position. Likewise, closing of the cover 2 causes the metering member 5 to move from its inhalation position backward to its filling position.

As already indicated above, during the movement of the metering member 5 from the filling position to the inhalation position as well as after the metering member 5 has reached its inhalation position, the dose of the powdered medicament filled in the dosing recess 15 is prevented from falling out by the protective member 7. The protective member 7 is slidable on the metering member 5 between its closed position, in which it covers the dosing recess 15, and its open position, in which it exposes the dosing recess 15 to the deagglomerator arrangement 10 and the inhalation channel 9 when the metering member 5 is in the inhalation position.

The protective member 7 is held in its closed position by the above-mentioned inhalation or breath actuated mechanism which is constructed such that the protective member 7 is moved from its closed position to its open position only if the inhalation suction force effected by the user in the inhalation channel 9 exceeds a predetermined level. Furthermore, the inhalation actuated mechanism is constructed such that only an inhalation suction breath, and not a blowing breath, can actuate the mechanism and can cause a movement of the protective member from its closed position to its open position.

FIG. 5 shows a more detailed perspective view of the inhalation actuated mechanism 18.

The inhalation actuated mechanism 18 comprises a sub-frame 8 which is shown in FIG. 4 only and holds a flap 20 acting as an inhalation actuated member, a coupling member 30, preferably in the form of a yoke, and a resilient member 40, preferably in the form of a drive spring. The resilient member 40 and the coupling member 30 are provided to drive the protective member 7 and to actuate a dose counting unit which comprises according to FIG. 5 a units wheel 12 having drive teeth 16 and a tens wheel 13 having drive teeth 17, which are coupled by an idler wheel (not shown). The units wheel 12 and the tens wheel 13 display the number of doses remaining in the container 4.

As shown in FIG. 5, recesses 11 are formed at the front corner portions of the metering member 5, and at one of these recesses 11 a prolonged end 43 of the resilient member 40 engages with the metering member 5 if the metering member is moved forward. By the contact with the metering member 5, the resilient member 40 is tensioned and charged up. A first end 41 of the resilient member 40 rests at a portion 21 of the flap 20 when the resilient member 40 is in its discharged state and normally holds the flap 20 in a first position, i.e., in a horizontal position. Therefore, by charging up the resilient member 40 by opening the cover 2, the reset force exerted by the first end 41 on the flap 20 is released.

In exemplary FIGS. 4 and 5, the upper surface of the flap 20 has an optional flag 22 which acts as a mark that is visible through openings in the upper side of the mouthpiece region of the powder inhaler and indicates that a dose is ready for inhalation. Furthermore, the flap 20 is coupled to the coupling member 30 via an arm portion 34 thereof and comprises one or two projections 23 acting as a counterweight. This counterweight balances the flap 20 and does not only reduce the actuation force required but also the susceptibility of the mechanism to accidental triggering.

As shown in FIG. 5, the resilient member 40 has a second end 42 which rests on a lateral side surface of the coupling member 30. The resilient member 40 is mounted on a shaft-like portion of the coupling member 30. At the opposite side thereof, the coupling member 30 has a projection 31 with a thickening 32 for operating the dose counting mechanism. From the bottom of the coupling member 30, there extends a prolongation 33 which engages with an opening 14 formed in the protective member 7 and with a slit (not shown in figures, as covered by the protective member 7) formed in the front end portion of the metering member 5.

When the flap 20 is held by the resilient member 40 in the horizontal position shown in FIG. 5, the protective member 7 prevents the powdered medicament contained in the dosing recess 15 from being displaced from the deagglomerator arrangement 10 if the user blows into the mouthpiece 3. Furthermore, the flap 20 provides a resistance if the user blows into the device giving positive feedback. If, however, the metering member 5 is pushed forward by opening the cover 2, the resilient member 40 is compressed and charged, and the reset force exerted by the end 41 on the flap 20 is released, so that the flap 20 can pivot or rotate from the horizontal first position into a second position that is pivoted downward relative to the horizontal first position if there is a sufficient high inhalation suction force in the inhalation channel 9. In the latter case, the movement of the flap 20 into its second position releases the arm 34 of the coupling member, which enables the resilient member 40, due to its compression, to move its second end 42 and thus the coupling member 30 slightly upward. By this rotational upward movement of the coupling member 30 the prolongation 33 extending from the lower side of the coupling member 30 moves forward, thereby moving the protective member 7 from its closed position to its open position and exposing the dosing recess 15 to the inside of the deagglomerator arrangement (cyclone) 10, so that the dose of the powdered medicament can be inhaled through the deagglomerator arrangement 10 and the inhalation channel 9 as well as the mouthpiece 3. In the cyclone or deagglomerator arrangement, the powdered medicament is entrained into a swirling airflow where the active part of the formulation is disaggregated from the carrier.

In exemplary FIGS. 4 and 5, since the flap 20 has been moved to its second position, the optional flag 22 will no longer be visible through the corresponding opening in the upper side of the mouthpiece, thereby indicating that a dose has been taken and that a new dose is not yet ready for inhalation.

Furthermore, as a result of this rotation of the flap 20 and the following clockwise rotation of the coupling member 30, the projection or cantilever 31 of the coupling member 30 is also slightly moved clockwise along the inclination of a next drive tooth 16 of the units wheel 12 so as to bring the thickening 32 into engagement with the respective drive tooth 16.

After inhalation, when the user closes the cover 2 again, the metering member 5 is moved backward to the filling position underneath the container 4, and this backward movement causes a counterclockwise rotation of the coupling member 30 as the prolongation 33 thereof is moved backward with the metering member 15. The counterclockwise rotation of the coupling member 30 is supported by the resilient member 40 which is allowed to be discharged and decompressed upon backward movement of the metering member 5. Due to this counterclockwise rotation of the coupling member 30, the projection 31 is also rotated counterclockwise, thereby rotating the units wheel 12 counterclockwise by one step which decreases the displayed number of doses left in the container 4.

Since the coupling member 30 and the resilient member 40 are moved back into their initial positions, the first end 41 of the resilient member 40 urges the flap 20 back into the horizontal position shown in FIG. 4 and FIG. 5. Moreover, the coupling member 30 is then again held by the engagement of its arm 34 with the flap 20, so that the whole powder inhaler has then been transferred into its initial position again.

SUMMARY

Starting from this structure and functionality of the inhalation actuated mechanism described above, it is the object of the present invention to provide a new flap design that allows to reduce the inhalation force required for activating the inhalation actuated mechanism and thus contributes to an improved performance of the corresponding powder inhaler.

According to the present invention, this object is achieved by a flap for an inhalation actuated mechanism of a powder inhaler as defined in claim 1 and a corresponding powder inhaler as defined in claim 15. The dependent claims define preferred and/or advantageous embodiments of the invention.

The flap of the invention comprises a base member, a skirt structure projecting from a surface of the base member, and a coupling portion to be coupled to a resilient member of a corresponding inhalation actuated mechanism of a corresponding powder inhaler.

The new flap design with the skirt structure or frame structure formed at the upper surface of the base member has an improved interaction with the powder inhaler chassis and an improved sealing of the casework and the flap to internal airflows, thereby allowing an improved device performance. Due to the new flap design, the inhalation flow rate required for the activation of the breath actuated mechanism of the inhaler can be reduced, and an improved inter- and intra-device reproducibility for the through life of the powder inhaler can be achieved, resulting also in an overall increase in the robustness of the powder inhaler while ensuring manufacturing capability. For example, with the new flap design, the mean breath actuated mechanism activation flow rate (BAM-AFR) can be reduced to a value in the range of 25 l/min, while the previous flap design required a mean BAM-AFR in the range of 38 l/min. The new flap design allows to achieve a very low variability of the activation flow rates for the through life of the powder inhaler, which may be in the range of 20 to 32 l/min. Thus, the inhalation actuated mechanism of the invention can be activated already at very low inspiratory flows which can be exerted more easily by patients that are affected by obstructive pulmonary airway diseases, such as asthma and COPD, for example. The addition of the skirt creates a labyrinth between the mouthpiece of the powder inhaler and the flap, which provides an increased resistance to air. This increased resistance makes the trigger flow more repeatable and reproducible without the inclusion of this labyrinth seal about the cover of the powder inhaler causing an increase in torque required to open and close the cover.

According to the preferred embodiment, the base member of the flap comprises a flat portion from which the skirt projects and a front end of the flat portion is at least partly rounded.

The flat portion may have a first longitudinal side and a second longitudinal side, the first and second longitudinal sides being connected by a combination of a straight front end portion and a rounded front end portion. A length of the first longitudinal side may be shorter than a length of the second longitudinal side.

According to an embodiment of the invention, the skirt comprises first side wall portions, which substantially extend in a longitudinal direction of the base member, and a second side wall portion which extends between the first side wall portions in a width direction of the base member and may comprise an elongate thickening in a middle portion thereof.

The first side wall portions are spaced from one another in the width direction of the base member and are preferably wedge-shaped such that a height of the first side wall portions gradually increases from a front end of the base member towards a rear end of the base member. The transverse second side wall portion may be inclined towards a rear end of the base member.

The coupling portion, interacting with the resilient member, preferably in the form of a spring, of the inhalation actuated mechanism may extend from a surface of the base member which is opposite to the surface from which the skirt projects.

According to an embodiment of the invention, the flap comprises a wing-shaped projection that projects from the flap backwards and is designed such that it acts as a counterweight upon a rotation of the flap in the inhalation actuated mechanism.

In the preferred embodiment, the flap comprises a portion to be coupled to a coupling member, preferably in the form of a yoke, of the inhalation actuated mechanism, the coupling member being provided for coupling the inhalation actuated mechanism with a protective member of a metering member of the powder inhaler. This coupling member may also be provided for actuating a dose counting mechanism of the powder inhaler.

The flap of the present invention may preferably be used in an inhalation actuated mechanism of the type disclosed in EP 1 386 630 B1. The further configuration of the corresponding powder inhaler of the present invention and the functionality of the corresponding components may be similar or even identical to the powder inhaler known from EP 1 386 630 B1.

In the following, a preferred embodiment of the invention will be described with reference to the drawing.

BRIEF DESCRIPTION OF THE DRAWINGS

FIG. 1A shows a perspective view of an inhalation actuated mechanism using a flap according to an embodiment of the invention before having been actuated by inhalation, FIG. 1B shows a perspective view of the inhalation actuated mechanism of FIG. 1A after it has been actuated by inhalation, and FIG. 1C shows a perspective view from a different side of an alternative embodiment of an inhalation actuated mechanism after inhalation has occurred.

FIG. 3A shows a first perspective side view of the flap similar to FIG. 2, FIG. 3B shows a second perspective side view of the flap, FIG. 3C shows a top view of the flap, FIG. 3D shows a first side view of the flap, FIG. 3E shows a second side view of the flap, FIG. 3F shows a bottom view of the flap, and FIG. 3G shows a rear view of the flap.

DESCRIPTION OF SPECIFIC EMBODIMENTS

Figure 1A:
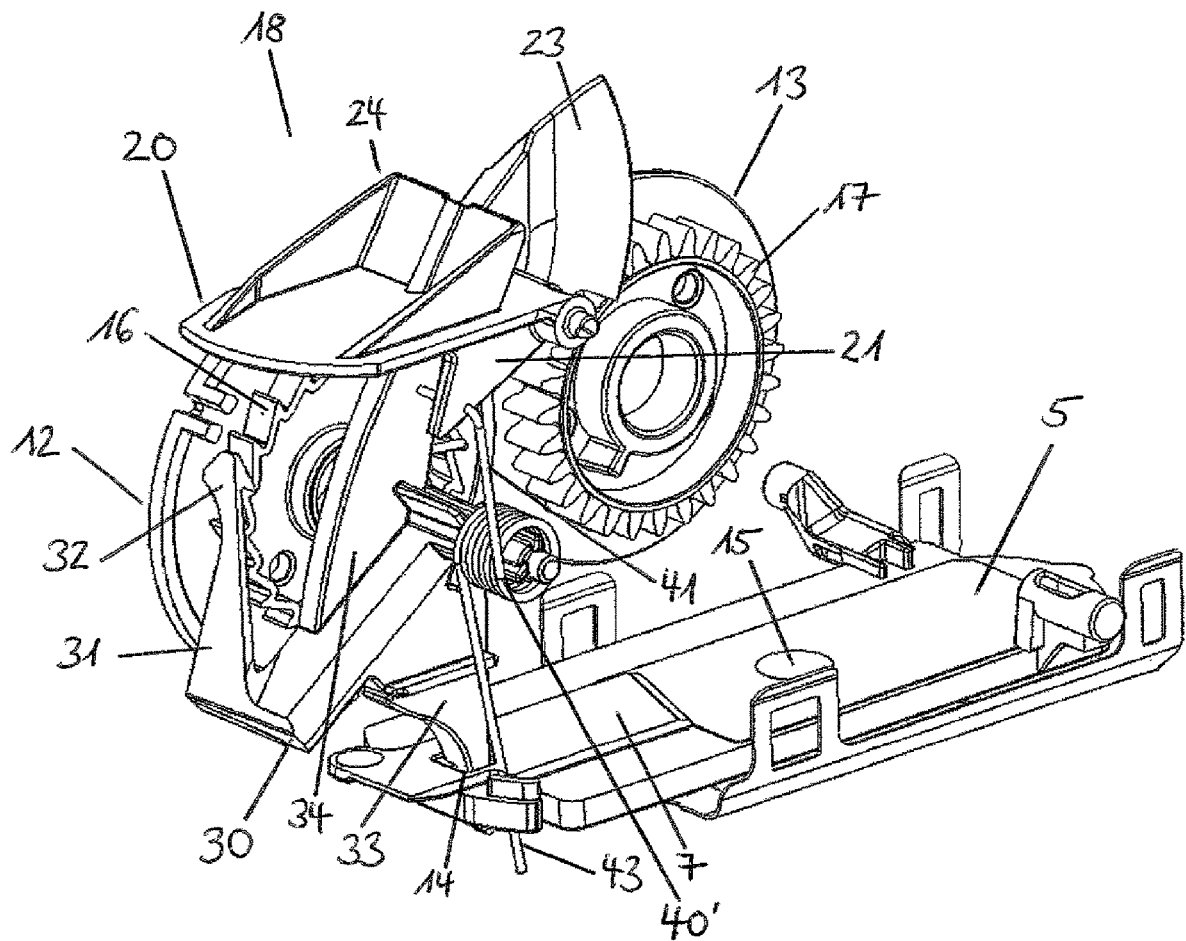
FIGS. 1A-1C show several perspective views of inhalation actuated mechanisms using a flap according to embodiments of the invention. In particular.

FIG. 1A shows an inhalation actuated mechanism 18 comprising a flap 20 acting as an inhalation actuated member, a coupling member 30 in the form of a yoke, and a resilient member 40' in the form of a drive spring attached to a shaft portion of the coupling member 30. The resilient member 40' has a similar function as the resilient member 40 shown in FIG. 5, but is different from the resilient member 40 in its shape. Therefore, as regards the functionality of the resilient member 40', in general reference can be made to the above explanations regarding the resilient member 40 shown in FIG. 5. The resilient member 40' and the coupling member 30 are provided to drive a protective member 7 for a dosing recess 15 of a metering member 5 of a corresponding powder inhaler and to actuate a dose counting unit which comprises according to FIG. 1A a units wheel 12 and a tens wheel 13. The units wheel 12 and the tens wheel 13 display the number of doses remaining in a medicament container of the powder inhaler or the number of doses that have already been taken. Drive teeth 16 of the units wheel 12 are coupled through a gear mechanism (not shown) with drive teeth 17 of the tens wheel 13. According to this particular embodiment, as shown in FIG. 1A, the first resilient member 40' engages with its prolonged end 43 with a recess of the metering member 5 and rests with its end 41 at a coupling portion 21 of the flap 20.

Figure 2:
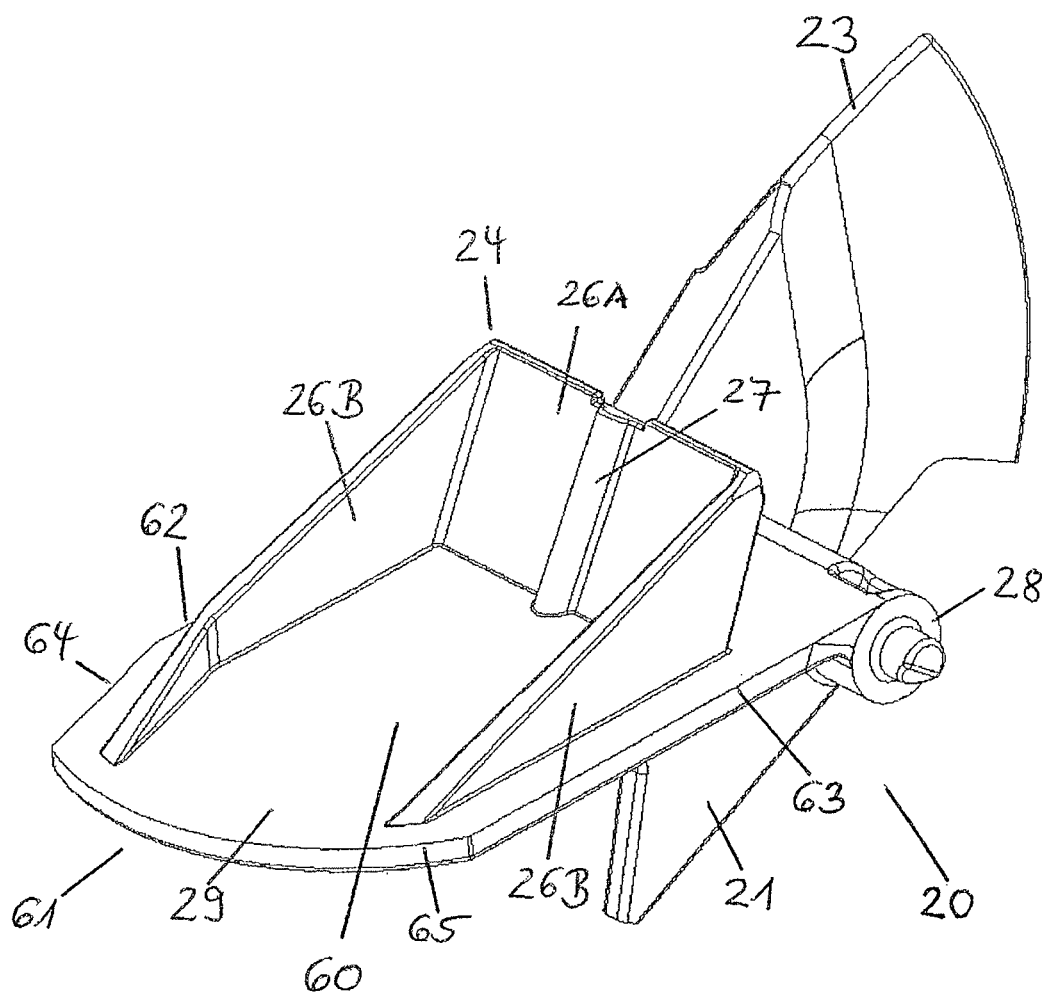
FIG. 2 shows an enlarged perspective view of the flap shown in FIGS. 1A-1C.

FIG. 2 shows an enlarged perspective view of the flap 20, and FIGS. 3A-3G show different further views of the flap 20.

According to the embodiment depicted in FIGS. 2 and 3A-3G, the flap 20 comprises a base member 29 with a substantially plate-shaped flat portion 60 from which a skirt or frame structure 24 projects upward. The skirt extends along the circumference of the base portion 29, but is open toward the front. The coupling portion 21 to be coupled to the resilient member 40' of the inhalation actuated mechanism 18 projects from the lower surface of the base portion 29 downward. Furthermore, the base member 29 comprises a shaft portion 28 at a rear end of the flat portion 60, the shaft portion 28 being provided to pivotably or rotatably support the flap 20 in the inhalation actuated mechanism 18 within the casing of the corresponding powder inhaler.

The front end 61 of the flat portion 60 of the base member 29 is at least partly rounded. According to the preferred embodiment, the flat portion 60 has a first longitudinal side 62 and a second longitudinal side 63, the first and second longitudinal sides 62, 63 being connected by a combination of a straight front end portion 64 and a rounded front end portion 65, and the length of the first straight longitudinal side 62 of the base member 29 is somewhat shorter than the length of the second straight longitudinal side 63, which can be best seen in the top and bottom views of FIG. 3C and FIG. 3F.

The skirt structure 24 comprises first side wall portions 26B, which substantially extend in a longitudinal direction of the base member 29, and a second side wall portion 26A which extends between the first side wall portions 26B in a width direction of the base member 29. The second side wall portion 26A comprises an integrated elongate thickening 27 extending from the base member 29 upward in a middle portion of the second side wall portion 26A.

In the preferred embodiments shown in FIGS. 1-3, the two first side wall portions 26B are spaced from one another in the width direction of the base member 29 and are wedge-shaped such that a height of the first side wall portions 26B gradually increases from a front end of the base member 29 towards a rear end of the base member 29. The second side wall portion 26A is slightly inclined towards the rear end of the base member 29 (see FIG. 3C, for example).

The first side wall portions 26B extend along the first and second longitudinal sides of the flat portion of the base member 29. That first side wall portion 26B, which extends along the first longitudinal side of the flat portion of the base member 29, i.e., the left side wall portion 26B, is angled such that a part thereof extends substantially parallel to the straight front end portion of the base member 29. The other first side wall portion 26B, i.e., the right side wall portion in FIG. 2, extends completely along a straight line.

As already described above, the preferably plate-shaped coupling portion 21 of the inhalation actuated mechanism 18 extends from a surface of the base member 29 which is opposite to the surface from which the skirt 24 projects. A further projection 23 projects from the shaft portion 28 of the flap 20 backward and is wing-shaped and designed such that it acts as a counterweight upon rotation of the flap 20 in the inhalation actuated mechanism 18. The projection 23 and the coupling portion 21 are spaced in a width direction of the flap 20 and extend substantially parallel to one another, which can be seen best in FIG. 3G.

Figure 3C:
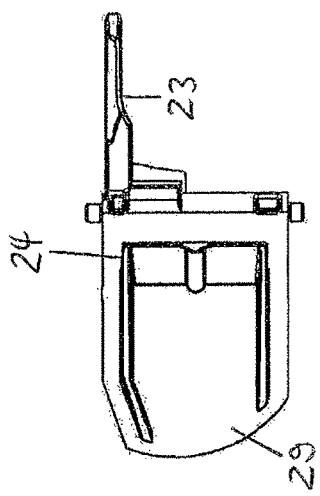
FIGS. 3A-3G shows several views of the flap. In particular.
Figure 3G:
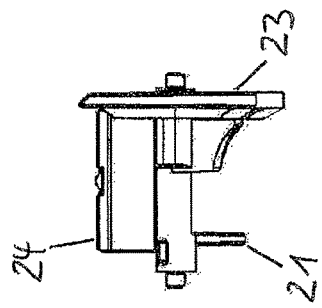
Figure 3B:
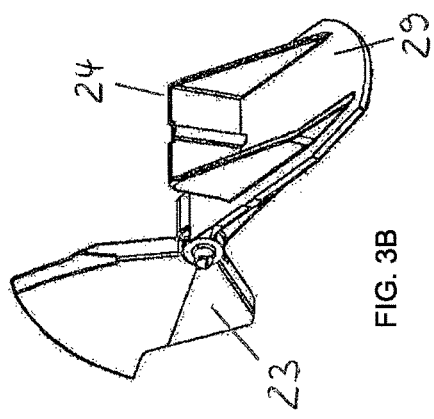
Figure 3F:
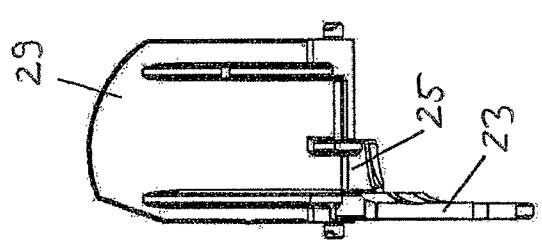
Figure 3A:
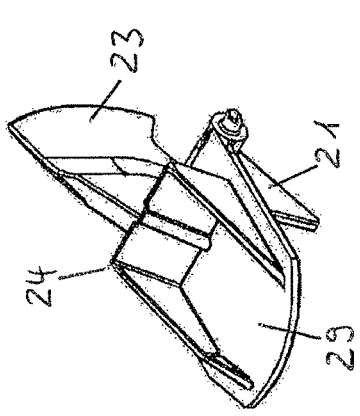
Figure 3D:
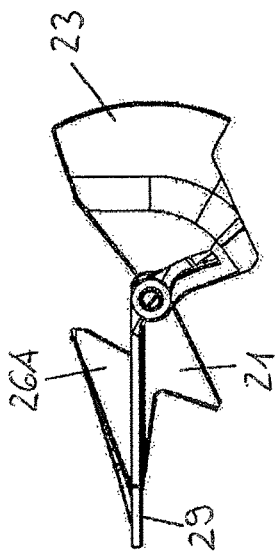
Figure 3E:
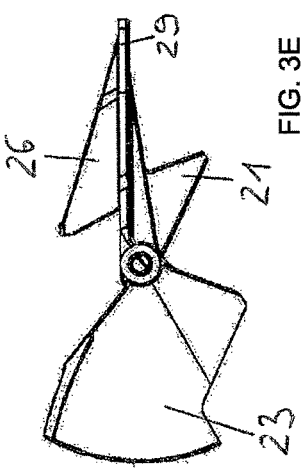

The flap 20 also comprises a portion 25 to be coupled to the coupling member 30 of the inhalation actuated mechanism 18 (see FIG. 3F).

Figure 4:
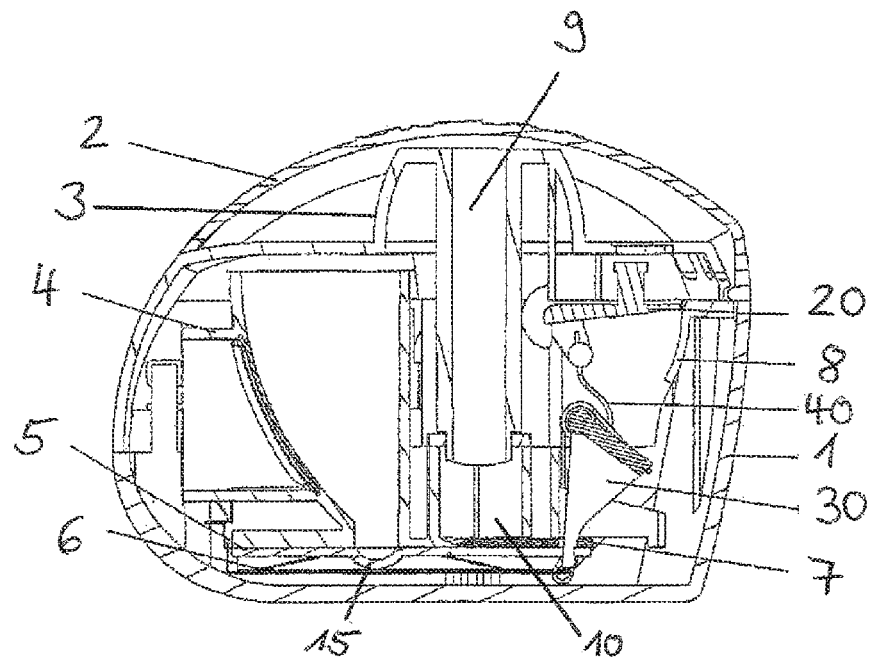
FIG. 4 (PRIOR ART) shows a cross-sectional view of a conventional powder inhaler in which the flap and the inhalation actuated mechanism of FIGS. 1-3 may be used.

The inhalation actuated mechanism 18 comprising the flap 20 may be used in a powder inhaler similar to that shown in FIG. 4, so that reference can be made to the above description with respect to the structure and functionality of the powder inhaler. In particular, the functionality of the inhalation actuated mechanism 18 is similar to that described in connection with FIG. 5.

As shown in FIG. 1A, an end 43 of the resilient member 40' engages with a front corner portion of the metering member 5 as the metering member is moved forward. By the contact with the metering member 5, the resilient member 40' is tensioned and charged up. A further end 41 of the resilient member 40' is coupled to the coupling portion 21 of the flap 20 such that, when the resilient member 40' is in its discharged state, the flap 20 is held in a first horizontal position. Therefore, by charging up the resilient member 40', this reset force exerted by the end 41 on the flap 20 is released.

Furthermore, the flap 20 is coupled at its lower surface at the portion 25 (see FIG. 3F) to a projection 34 of the coupling member 30 and comprises the wing-shaped further projection 23 which acts as a counterweight and projects backward from the shaft portion 28 of the flap 20. This counterweight balances the flap 20 and does not only reduce the actuation force required but also the susceptibility of the mechanism to accidental triggering.

As shown in FIG. 1A, the resilient member 40' is mounted on a shaft-like portion of the coupling member 30. At the opposite side thereof, the coupling member 30 has a projection 31 with a thickening 32 for operating the dose counting mechanism. From the bottom of the coupling member 30, there extends a prolongation 33 which engages with an opening 14 formed in the protective member 7 and with a slit (not shown) formed in the front end portion of the metering member 5.

When the flap 20 is held by the resilient member 40' in the horizontal position shown in FIG. 1A, the protective member 7 prevents the powdered medicament contained in the dosing recess 15 from being displaced from the deagglomerator arrangement of the powder inhaler if the user blows into the mouthpiece of the powder inhaler. Furthermore, the flap 20 provides a resistance if the user blows into the device giving positive feedback. If, however, the metering member 5 is pushed forward by opening the cover of the powder inhaler, the resilient member 40' is compressed and charged, and the reset force exerted by the end 41 on the flap 20 is released, so that, if there is a sufficient high inhalation suction force in the inhalation channel of the powder inhaler, the flap 20 can pivot or rotate from the horizontal first position into a second position that is pivoted downward relative to the horizontal first position. In the latter case, the movement of the flap 20 into its second position releases the portion 34 of the coupling member 30, which enables the resilient member 40', due to its compression, to move the coupling member 30 slightly upward. By this rotational upward movement of the coupling member 30 the prolongation 33 extending from the lower side of the coupling member 30 moves forward, thereby moving the protective member 7 from its closed position to its open position and exposing the dosing recess 15 to the inside of the deagglomerator arrangement (cyclone) of the powder inhaler, so that the dose of the powdered medicament can be inhaled through the deagglomerator arrangement and the inhalation channel as well as the mouthpiece.

Furthermore, as a result of this rotation of the flap 20 and the following clockwise rotation of the coupling member 30 due to the action of the resilient member 40', in cooperation with that of the second optional resilient member mounted on the shaft-like portion of the coupling member 30 at the opposite side with respect to the resilient member 40', the projection or cantilever 31 of the coupling member 30 is also slightly moved clockwise along the inclination of a next drive tooth 16 of the units wheel 12 so as to bring the thickening 32 into engagement with the respective drive tooth 16.

Figure 1B:
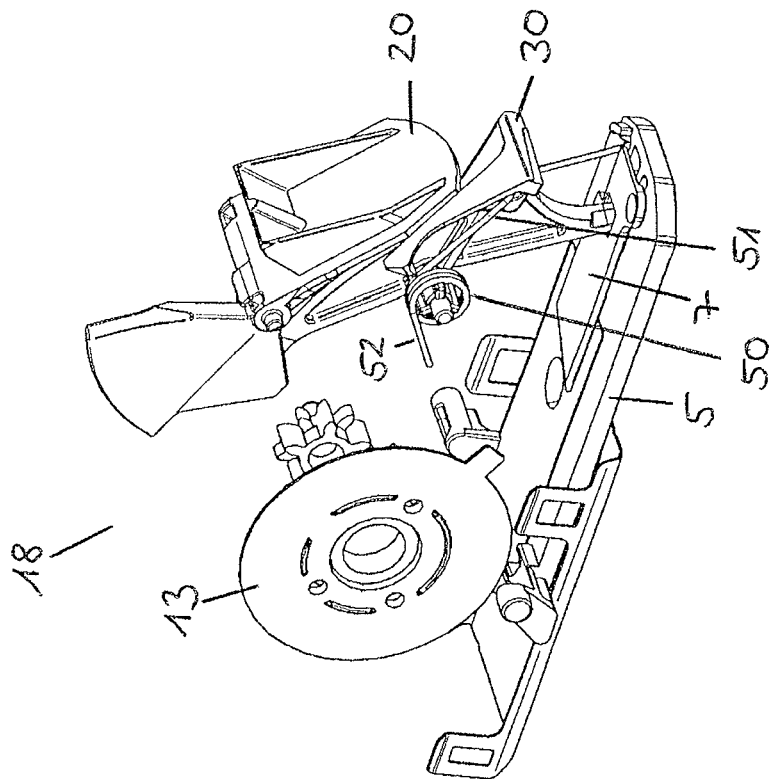

FIG. 1B shows a position of the inhalation actuated mechanism 18 after inhalation has occurred.

After inhalation, when the user closes the cover of the powder inhaler again, the metering member 5 is moved backward to the filling position underneath the medicament container of the powder inhaler, and this backward movement causes a counterclockwise rotation of the coupling member 30 as the prolongation 33 thereof is moved backward with the metering member 15. The counterclockwise rotation of the coupling member 30 is supported by the resilient member 40' which is allowed to be discharged and decompressed upon backward movement of the metering member 5. Due to this counterclockwise rotation of the coupling member 30, the projection 31 is also rotated counterclockwise, thereby rotating the units wheel 12 counterclockwise by one step which decreases the displayed number of doses left in the container 4.

Since the coupling member 30 and the resilient member 40' are moved back into their initial positions, the end 41 of the resilient member 40' urges the flap 20 back into the horizontal position shown in FIG. 1A. Moreover, the coupling member 30 is then again held by the engagement of its projection 34 with the flap 20, so that the whole powder inhaler has then been transferred into its initial position again.

Figure 1C:
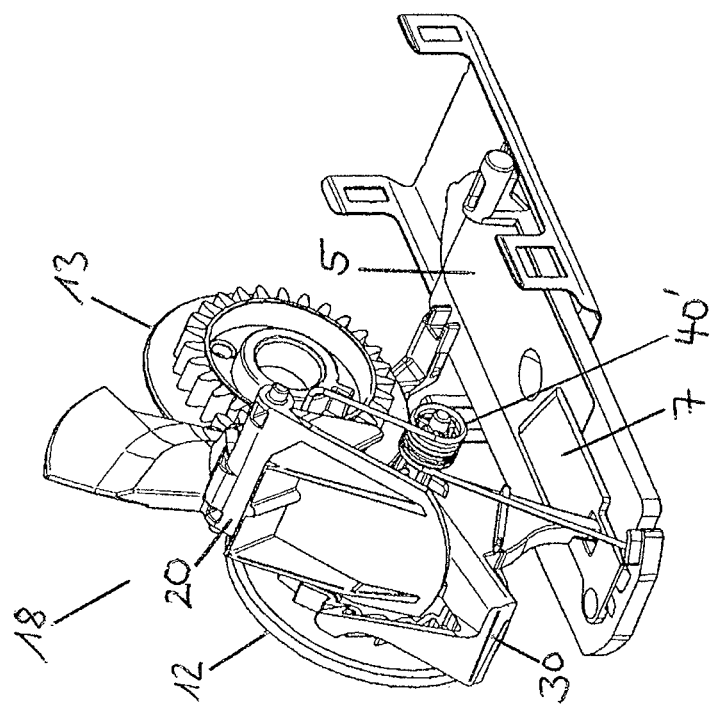

FIG. 1C shows a perspective view of an alternative embodiment of the inhalation actuated mechanism 18 from a different side. In FIG. 1C, the same components as those shown in FIGS. 1A and 1B are designated by the same reference numerals, and as regards the functionality of these components, reference can be made to the above explanations. It should be noted that, in the view of FIG. 1C, the units wheel 12 has been omitted for clarity reasons.

In this alternative embodiment, for imparting to the coupling member 30 a suitable force, which is released during inhalation, a second resilient member 50, mounted on the shaft-like portion of the coupling member 30, at the opposite side with respect to the resilient member 40', may be present. In particular, the second resilient member 50 may be provided in the form of a drive spring which at one end 51 interacts with an adjacent lateral side surface of the coupling member 30 and at the other end 52 rests on a surface positioned on a lateral portion of the chassis, close to a point wherein the shaft portion of the coupling member 30 is hinged to. The downward movement of the flap 20 during inhalation releases part of the force exerted by the second resilient member 50 on the coupling member 30, while the closing of the cover of the powder inhaler tensions the second resilient member 50.

Figure 5:
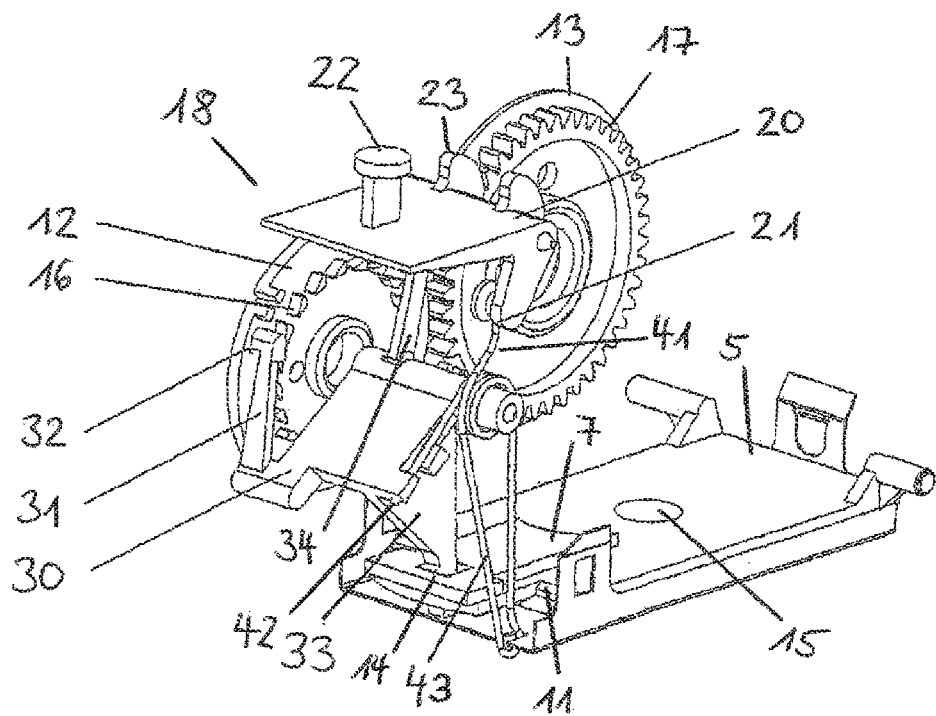
FIG. 5 (PRIOR ART) shows a perspective view of the inhalation actuated mechanism of the conventional powder inhaler of FIG. 4.

Although not shown in FIGS. 1A-1C and FIG. 2, similar to FIG. 4 and FIG. 5 the flap 20 may be provided with a flag 22 which acts as a mark that is visible through an opening in the mouthpiece 3 of the powder inhaler and indicates that a dose is ready for inhalation.

To confirm the advantages associated with the invention, a through life breath actuated mechanism activation flow rate (BAM-AFR) characterisation was performed. In particular, tests were carried on 66 devices, not containing the powder formulation, being provided with a breath or inhalation actuated mechanism with the new flap according to the invention and on corresponding 60 devices, not containing the powder formulation, being provided with a breath actuated mechanism with a previous flap design according to the prior art.

The method was similar to that described in the European Pharmacopoeia 8.0 for Inhalation Powders: Tests for Uniformity of Delivered Dose, and the equipment for performing the tests comprised a device handling unit rig provided with a device seat, to fix the device during the experiment and the following units connected in the following order: the mouthpiece of the device was connected to a Dose Unit Sampling Apparatus for dry powder inhalers (DUSA—Copley Scientific) through a suitable adapter, a HEPA (High Efficiency Particulate Air) filter, a flowmeter (Copley), and a Critical Flow Controller (TPK model—Copley Scientific), in its turn connected to a vacuum supply port. The DUSA was also connected to a manometer. Details on the working requirements of Copley instruments and apparatus (DUSA, flowmeter, Critical Flow Controller) known to the skilled in the art are also available in Copley Scientific Brochures available at the company web site.

After initial leak check and having sealed any potential leaks at connection points, the tests on the activation flow rate for each device and for the through life of each device were performed. Each device was exposed to a starting flow rate of 20.0 l/min to confirm whether the flap was activated or not. If the flap was not activated, the device was re-primed and retested at the flow rate increased by 2.5 l/min. If again the flap was not activated, then the flow rate was increased a further 2.5 l/min and retested. This continued until an activation of the flap was recorded, up to a maximum flow rate of 60 l/min. The flow rate at which the activation occurs was recorded as its BAM-AFR. This method was applied to five doses at the start of life of the device (from the $1^{st}$ to the $5^{th}$), and ten doses at the end of life of the device (from the $111^{th}$ to the $120^{th}$) with the intervening doses being shot to waste at a higher flow rate.

The powder inhalers provided with the flap design according to the invention resulted in a mean BAM-AFR of 25 l/min, while the powder inhalers with the previous flap design required a mean BAM-AFR of 38 l/min. The results therefore showed a large reduction in the BAM-AFR for the through life of the powder inhaler provided with the flap according to the present invention with respect to the powder inhaler provided with the flap design according to the prior art. Moreover the new flap design allowed to achieve a variability of the activation flow rates for the through life of the powder inhaler in the range of 20 to 32 l/min, which was very low with respect to the variability showed by the previous flap design.

The invention claimed is:

1. A flap for an inhalation actuated mechanism of a powder inhaler, comprising:
   a base member comprising a continuous plate-shaped flat portion;
   a skirt structure projecting upward from a surface of the flat portion of the base member; and
   a coupling portion to be coupled to a resilient member of the inhalation actuated mechanism, wherein:
   the skirt structure comprises first side wall portions, which substantially extend in a longitudinal direction of the flat portion of the base member,
   a second side wall portion which extends between the first side wall portions in a width direction of the flat portion of the base member, and
   the coupling portion projects from a lower surface of the flat portion of the base member downward.

2. The flap according to claim 1,
   wherein the base member comprises a shaft portion at a rear end of the flat portion, the shaft portion being provided to pivotably support the flap in the inhalation actuated mechanism.

3. The flap according to claim 1,
   wherein a front end of the flat portion is at least partly rounded.

4. The flap according to claim 1,
   wherein the flat portion has a first straight longitudinal side and a second straight longitudinal side, the first and second longitudinal sides being connected by a combination of a straight front end portion and a rounded front end portion.

5. The flap according to claim 4,
   wherein a length of the first longitudinal side is shorter than a length of the second longitudinal side.

6. The flap according to claim 1,
   wherein the second side wall portion comprises an elongate thickening extending from the base member in a middle portion of the second side wall portion.

7. The flap according to claim 1,
   wherein the skirt structure comprises two of the first side wall portions which are spaced from one another in the width direction of the base member and are wedge-shaped such that a height of the first side wall portions gradually increases from a front end of the base member towards a rear end of the base member.

8. The flap according to claim 1,
   wherein the second side wall portion is inclined towards a rear end of the base member.

9. The flap according to claim 4,
   wherein the first side wall portions extend along the first and second longitudinal sides of the flat portion of the base member.

10. The flap according to claim 9,
    wherein the first side wall portion that extends along the first longitudinal side of the flat portion of the base member is angled such that a part thereof extends substantially parallel to the straight front end portion of the base member.

11. The flap according to claim 1,
    wherein the flap comprises a projection that projects from a shaft portion of the flap backwards; and
    wherein the projection is configured to act as a counterweight upon a rotation of the flap in the inhalation actuated mechanism.

12. The flap according to claim 11,
    wherein the projection and the coupling portion are spaced in a width direction of the flap and extend substantially parallel to one another.

13. A powder inhaler, comprising:
    a container for storing a powdered medicament;
    a metering member having a dosing recess to be filled with a dose of the powdered medicament from the container;
    a mouthpiece being in communication with an inhalation channel for enabling inhalation of the dose of the powdered medicament contained in the dosing recess of the metering member; and
    an inhalation actuated mechanism which is coupled to a protective member for the dosing recess of the metering member such that, if the protective member is in a closed position in which it at least partly covers the dosing recess, the inhalation actuated mechanism causes the protective member to move to an open position, in which the protective member does not cover the dosing recess, if an inhalation suction force exerted by a user on the inhalation channel exceeds a predetermined value,
    wherein the inhalation actuated mechanism comprises the flap according to claim 1.

14. The powder inhaler according to claim 13,
    wherein the flap is arranged such that it is pivotable between a first position and a second position, wherein the flap is coupled to the protective member such that, if there is an inhalation suction force exceeding the predetermined value, the flap is moved from the first position to the second position, thereby causing the protective member to move from the closed position to the open position.

15. The powder inhaler according to claim 14,
    wherein the inhalation actuated mechanism comprises a resilient member which is configured to be tensioned by a movement of the metering member from a filling position, in which the dosing recess is in alignment with an opening of the container so as to be filled with the dose of the powdered medicament, to an inhalation position, in which the dosing recess is in alignment with the inhalation channel, wherein the resilient member is configured to be discharged upon a movement of the metering member from the inhalation position to the filling position;
    wherein the resilient member is arranged such that it holds the flap in its first position if the resilient member is discharged, while the resilient member releases the flap if the resilient member is tensioned, so as to allow the flap to be moved from its first position to its second position by the inhalation suction force exceeding the predetermined value.

16. The powder inhaler according to claim 15,
    wherein the inhalation actuated mechanism comprises a coupling member coupling the flap to the protective member with the resilient member being coupled to the coupling member; and
    wherein the coupling member comprises a portion which is configured to be held by the flap when it is in its first position, while the portion of the coupling member is configured to be released by a movement of the flap from its first position to its second position.

17. The powder inhaler according to claim 16,
    wherein the resilient member is a spring attached to a shaft-like portion of the coupling member.

18. The powder inhaler according to claim 16, wherein the inhalation actuated mechanism comprises a further resilient member which is mounted on a shaft-like portion of the coupling member.

19. The powder inhaler according to claim 18, wherein the further resilient member is a spring mounted on the shaft-like portion of the coupling member at an opposite side with respect to the resilient member.

20. The powder inhaler according to claim 19, wherein the further resilient member has a first end coupled to the coupling member and a second end coupled to a chassis of the powder inhaler.

\* \* \* \* \*